United States Patent
Fine et al.

(10) Patent No.: US 7,266,400 B2
(45) Date of Patent: Sep. 4, 2007

(54) GLUCOSE LEVEL CONTROL METHOD AND SYSTEM

(75) Inventors: Ilya Fine, Rehovot (IL); Lior Ma'Ayan, Ramat Hasharon (IL)

(73) Assignee: Orsense Ltd., Rehovot (IL)

( * ) Notice: Subject to any disclaimer, the term of this patent is extended or adjusted under 35 U.S.C. 154(b) by 419 days.

(21) Appl. No.: 10/429,969

(22) Filed: May 6, 2003

(65) Prior Publication Data
US 2004/0225205 A1 Nov. 11, 2004

(51) Int. Cl.
*A61B 5/00* (2006.01)
(52) U.S. Cl. ..................................... 600/316
(58) Field of Classification Search ........... 600/310, 600/316, 322, 323, 324, 326, 331, 483, 485
See application file for complete search history.

(56) References Cited

U.S. PATENT DOCUMENTS

| | | | |
|---|---|---|---|
| 5,068,536 A * | 11/1991 | Rosenthal | 600/316 |
| 5,485,838 A * | 1/1996 | Ukawa et al. | 600/330 |
| 5,822,715 A | 10/1998 | Worthington et al. | |
| 5,840,020 A | 11/1998 | Hinonen et al. | |
| 5,899,855 A * | 5/1999 | Brown | 600/301 |
| 6,213,952 B1 | 4/2001 | Finarov et al. | |
| 6,400,971 B1 | 6/2002 | Finarov et al. | |
| 6,400,972 B1 | 6/2002 | Fine | |
| 6,801,798 B2 * | 10/2004 | Geddes et al. | 600/323 |
| 6,840,904 B2 * | 1/2005 | Goldberg | 600/300 |

FOREIGN PATENT DOCUMENTS

| WO | WO 01/13786 A1 | 3/2001 |
|---|---|---|
| WO | WO 01/72208 A2 | 10/2001 |

OTHER PUBLICATIONS

Ingelfinger, Joseph A. et al., "Biostatistics in Clinical Medicine", New York: Macmillan Publishing Co., Inc., 1983, p. 116-121.

* cited by examiner

*Primary Examiner*—Eric F. Winakur
(74) *Attorney, Agent, or Firm*—Browdy and Neimark PLLC

(57) ABSTRACT

A method and device are provided for self-monitoring a patient's blood glucose condition to determine a long-term effect of the patient's behavior on his blood glucose level. A sequence of measurements of the blood glucose level is applied during a day, the sequential measurements are repeated during a predetermined time period from several days to several weeks, and measured data are collected. The measured data is analyzed to determine a distribution of the average glucose values within said predetermined time period, thereby providing a feedback for the patient or an authorized person.

10 Claims, 7 Drawing Sheets

$P_1 = 0$ $P_2 = 15\text{mmHg}$ $P_3 = 30\text{mmHg}$

P₄=45mmHg

P₅=55mmHg

P₆=65mmHg

P₇=90mmHg

P₈=130mmHg

GLUCOSE LEVEL CONTROL METHOD AND SYSTEM

FIELD OF THE INVENTION

This invention is generally in the field of glycemic management and relates to a method and system for controlling and monitoring blood glucose levels.

BACKGROUND OF THE INVENTION

Diabetes is a major source of morbidity, mortality and economic expenses in the most countries. Although people with diabetes can prevent or delay complications associated with the disease by keeping blood glucose levels close to normal, preventing or delaying the development of the disease in the first place is as simple and for many researchers it is a sought after result.

Self-management has been shown to reduce the costs associated with diabetes. Improving glycemic control naturally results in improved quality of life, higher retained employment, greater productive capacity and less absenteeism. Numerous studies have shown that the most effective method of preventing long term complications of diabetes is by maintaining normal blood glucose levels. However, the on set of the disease could never be predicted. The majority of healthy people have no sigh or symptoms associated with diabetes. Symptoms can be so mild that even those actually suffering from the disease would not be aware of their condition until a complication of the disease erupts. Early detection of the disease has, therefore, been the holly grail of the diabetic research.

However, early detection of the disease could not simply rely on long term monitoring of blood glucose levels and would require analysis of the log term effects of everyday activities such as diet, physical activities and medications. By the same token, immediate monitoring of blood glucose by way of finger-stick test would not be effective in early detection of the disease or in controlling and maintaining normal blood glucose levels.

Thus, patients already suffering from diabetes and healthy individuals who are at risk face a problem of maintaining strict glycemic control in order to decrease the risk of complications or acquiring the disease. A major challenge is the creation of a simple and reliable non-invasive method for self-monitoring which relies on periodic measurements and which is capable of providing the patient and/or the physician with short-term information regarding the patient's glycemic management.

It is also highly recommended by the medical profession that insulin-treated individuals practice self-monitoring of blood glucose. Based on the level of glucose in the blood, the individual may take insulin dosage adjustments before injection. Adjustments are necessary since blood glucose levels vary on a daily basis for a variety of reasons. Despite the importance of self-monitoring, the proportion of individuals who self-monitor at least once a day declines significantly since obtaining blood from the finger is painful and often results in infection and formation of hard scar tissue.

One of the most clinically important sources of information regarding the blood-glucose levels of an individual comes from monitoring said individual for glycohemoglobin or hemoglobin $A_{1c}$ (Ab$A_{1c}$) level. An Hb$A_{1c}$ result reflects the glucose concentration over the previous two to three months as weighted mean during that time. The Hb$A_{1c}$ is used as an overall measure of extended glycemic control.

The utilization of the invasive Hb$A_{1c}$ method in the prediction of blood glucose behavior is disclosed in International Publication WO 01/72208. Here, a method, a system and a computer program is disclosed for predicting the long term risk of hyperglycemia and the long-term and short-term risks of sever hyperglycemia in diabetes, based on glucose readings collected by a self-monitoring blood glucose device. The method and the system of the disclosed invention pertain directly to the enhancement of existing home blood glucose monitoring devices by introducing an intelligent data interpretation component capable of predicting both Hb$A_{1c}$ and periods of risk of hyperglycemia.

WO 01/13786 discloses a method which utilizes blood glucose sampling, insulin infusion/injection records, heart rate information and heart rate variability information to predict blood glucose levels and the onset of hypoglycemia in the near future based on an assessed risk of hypoglycemia. This technique also provides for predicting blood glucose levels and for assessing the risk of the onset of hypoglycemia in the near future.

The assessment or prediction of the onset of hypoglycemia or hyperglycemia, nevertheless, is not relevant when it comes to individuals who are at high risk of developing diabetes or to patients suffering from the disease for whom self-monitoring is the preferred method.

U.S. Pat. No. 5,840,020 to Heinonen et al, disclose a method of such self-monitoring which comprises formulating an adaptive mathematical model about the behavior of a patients glucose level, the model taking into account the patient's diet, medication, and physical strain and comprising comparing the predictive values provided by the model to the measured glucose level.

A diabetes management system for predicting future blood glucose concentrations based upon current blood glucose concentrations and the insulin action remaining from previous insulin doses has been proposed in U.S. Pat. No. 5,822,715 to Worthington.

SUMMARY OF THE INVENTION

There is a need in the art to facilitate patients suffering from diabetes and those individuals who are at risk of developing the disease to obtain data indicative of the variations in blood glucose condition, by providing a novel self-monitoring method and system.

The inventors have found that data indicative of the distribution of an average blood glucose condition of a patient within a certain period of time is an important factor for the purposes of evaluating how the patient's everyday activities analyzing measured data of blood glucose condition several times a day over a period from several days to several weeks is sufficient for a patient to self-obtain data indicative of the average blood glucose condition and distribution of the average value. The patient himself can thus arrive to a conclusion that his activity is to be changed and/or he needs a physician's involvement.

The technique of the present invention utilizes sequential non-invasive measurements of blood glucose levels at least five times a day, either spontaneously or at times prior/after physical activity or prior/after meals or while having changed in his routine every day behavior, i.e., changing diet or medication. The result of such long-term sequential measurements is data indicative of a distribution of the average glucose level within a certain time period that provides a feedback for the patient or physician.

Thus, according to a broad aspect of the invention, there is provided a method of self-monitoring a patient's blood glucose condition to determine a long-term effect of the patient's behavior on his blood glucose level, the method comprising: applying a sequence of measurements of the blood glucose level during a day, repeating the sequential measurements during a predetermined time period from several days to several weeks and collecting measured data; analyzing the measured data to determine a distribution of the average glucose values within said predetermined time period, thereby providing a feedback for the patient or an authorized person.

To improve the quality of measurements, a measurement device used for said sequential non-invasive measurements can be calibrated by utilizing a value of glucose concentration in blood of a specific patient obtained with a reference measurement taken by another, more precise measurement device (invasive or non-invasive) and the measured data obtained from at least one of said non-invasive measurements taken just prior to or after the reference measurement. The reference measurement and the corresponding non-invasive measurement (i.e., that taken prior to or immediately after the reference measurement) are then analyzed to correlate between them, a suitable statistic algorithm is used to optimize the coefficients (variables) of the non-invasive measurement to obtain the best fitting, and the final decision is taken upon meeting a certain quality criteria.

By applying numerous reference measurements and corresponding non-invasive measurements to blood of the same patient, a calibration function can be calculated. This calibration function can be further updated by utilizing data indicative of periodically (or sporadically) taken more precise measurements (invasive or non-invasive), and the updated calibration function is used upon carrying out a further non-invasive measurement.

Thus, according to another aspect of the invention, there is provided a method of calibrating a non-invasive measurement device for use in self-monitoring a patient's blood glucose condition, the method comprising:

using a first measurement device, of a kind different from said non-invasive measurement device, to obtain first measured data indicative of glucose concentration in the patient's blood;

applying said non-invasive measurement device to said patient either prior to or after said first measurement, said non-invasive measurement device utilizing a certain calculation model to determine second measured data indicative of the glucose concentration in the patient's blood;

determining a correlation between said fast measured data and said second measured data, and applying a medical statistic algorithm to thereby optimize coefficients used in said model to obtain the best fitting between the first and second measured data.

According to yet another aspect of the invention, there is provided a measurement device for use in self-monitoring a patient's blood glucose condition, the device comprising: a measurement unit operable for detecting data indicative of a blood glucose level, and a control unit (processor unit) connectable to the measurement unit for collecting and analyzing the measured data to determine a distribution of the average glucose values within a predetermined time period, thereby providing a feedback for the patient or an authorized person about a long-term effect of the patient's behavior on his blood glucose level.

Preferably, the sequentially applied non-invasive measurements are the so-called "occlusion-based" measurements utilizing the technique disclosed in U.S. Pat. No. 6,400,972 assigned to the assignee of the present application. Generally, this technique consists of the following. A condition of artificial kinetics is created at a measurement location in the patient's blood perfused fleshy medium (for example by applying an over-systolic pressure to the medium) thereby causing the state of temporarily blood flow cessation, and then optical measurements are applied to the medium while at the state of the blood flow cessation. A relation between the time variations of two light responses of the medium corresponding to predetermined different wavelengths of incident light is indicative of the glucose concentration in the patient's blood. Thus, the measuring unit comprises a pressurizing assembly operable to controllable apply pressure to an appropriate location on the patient's body, and optical system including a multi-wavelength illuminator (generally, at least two wavelengths) and a light detector.

While using a glucose-meter in the form of an optical measurement device based on the application of pressure, for example the above-described occlusion-based measurement device, the same device provides for measuring also the patient's blood pressure. The blood pressure measurements consist of applying to the medium gradually increasing pressure from under-systolic to over-systolic pressure and concurrently applying optical measurements to detect the time variation of a light response of the medium, thereby obtaining the light response as the function of time and the applied pressure. During the application of pressure, the light response profile (i.e., time variation of the light response) changes from the pulsatile profile to substantially non-pulsatile profile. The pressure corresponding to the light response profile still having pulsatile components but with a changed form (as compared to that of the lower pressure values) is the diastolic pressure, and that corresponding to the disappeared pulsatile components is the systolic pressure.

Thus, according to yet another broad aspect of the invention, there is provided a method for measuring a patient's blood pressure, the method comprising:

applying to the patient's blood perfused fleshy medium a gradually increasing pressure, and concurrently applying an optical measurements to the medium to determine a time variation of a light response of the medium as a function of the applied pressure;

analyzing the measured time variations of the light response as the function of the applied pressure to determine a diastolic pressure as the pressure corresponding to an appearance of a changed form of the time variation of the light response while having pulsatile components and determine a systolic pressure as the pressure corresponding to substantial disappearance of the pulsate components in the time variation of the light response.

According to yet another aspect of the invention, there is provided a non-invasive measurement device for determining both the glucose concentration in patient's blood and the patient's blood pressure, the device comprising:

an optical measurement system for applying to the patient's blood perfused fleshy medium, said system including an illuminator producing light of at least two different wavelengths, and a light detector for detecting light responses of the medium at the different wavelengths and generating measured data indicative thereof;

a pressurizing assembly operable to apply pressure to the medium; and a control unit operating the pressurizing assembly to apply pressure gradually increasing from under-systolic to over-systolic pressure, and maintaining the over-systolic pressure during a certain time period, and operating the measurement system to apply measurements and generate the measured data during the application of pressure, the control unit having a data processing and analyzing utility operable to analyze the light responses and determine a diastolic pressure as the pressure corresponding to an appearance of a changed form of the light response while having pulsatile components, determine a systolic pressure as the pressure corresponding to substantial disappearance of the pulsatile components in the light response, and determine the glucose concentration from a relation between the time variations of the light responses at the different wavelengths measured during the application of the over-systolic pressure.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
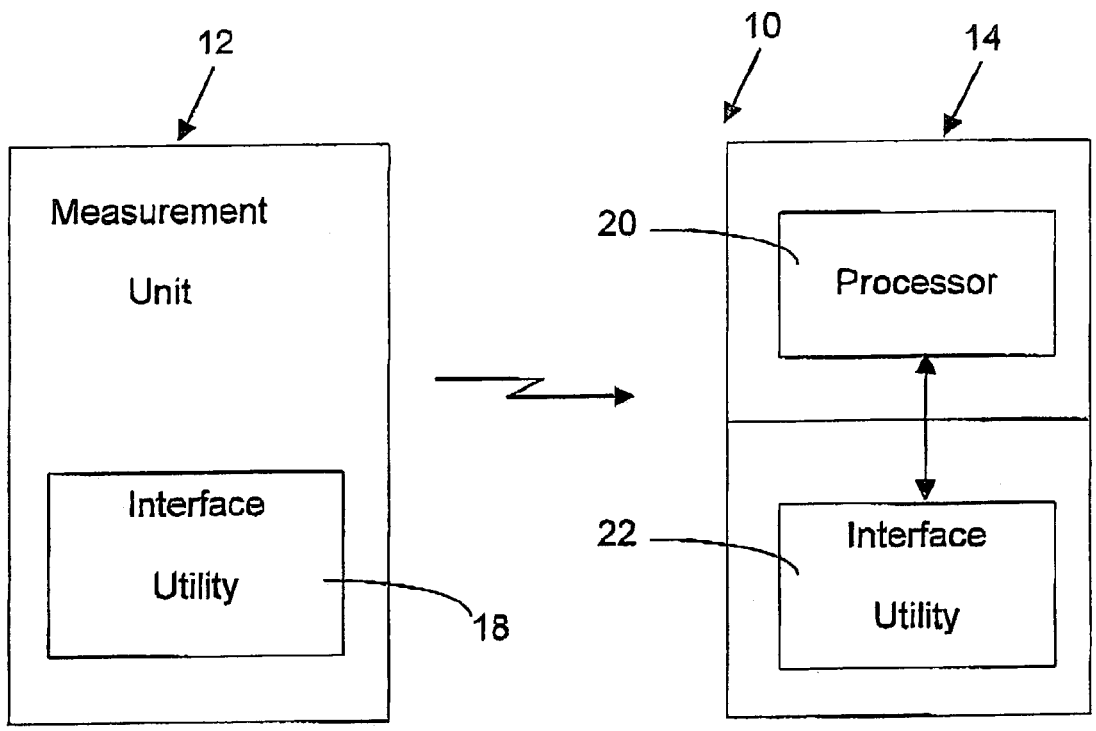
FIG. 1 is a schematic block diagram of a measurement device suitable to be used in a method according to the invention for self-monitoring a patient's blood glucose condition.

Referring to FIG. 1, there is illustrated a measurement device 10 suitable to be used in the technique of the present invention. The device comprises such main constructional parts as a measurement unit 12 and a control unit 14 connectable to each other via wires or wirelessly (by using IR, RF or acoustic signaling). The control unit 14 may be a separate computer device, part of the patient's personal computer (e.g., PALM), or integral processor utility of the measurement unit.

The measurement unit 12 is any known glucose-meter (such as ACCU-CHECK commercially available from Rosch company), or the optical measurement device disclosed in U.S. Pat. Nos. 6,213,952; 6,400,971; and 6,400,972, all assigned to the assignee of the present application. The measurement unit is preferably equipped with an interface utility 18 designed to enable input from a patient to initiate a measurement session and entry data indicative of moment and/or condition of a specific measurement session. This data may include time of day or kind of activity undertaken prior to or during the measurement session.

For example, the patient may decide to periodically take measurements during a day at a certain predefined period. In this case, the device 10 may be in the so-called "automatic measurement mode", i.e., the measurement unit 12 is designed to be continuously carried by a patient in a measurement position and either the measurement unit 12 or the control unit 14 is preprogrammed to timely initiate the periodic measurement sessions.

The measurement unit may for example be designed like a finger clip, or a wristwatch, which is preferred in the above-described example of automatic periodic measurements.

The control unit 14 inter alia includes a processor utility 20 and an interface utility 22. The processor utility 20 is preprogrammed to collect measured data from the measurement unit and carry out data analysis consisting of determining a distribution of blood glucose levels as a function of a certain parameter selected by the patient and entered via the interface utility 22. For example, the patient might desire to determine the time periods of hyper- or hypoglycemic events, the daily average glucose levels during a predetermined period of time, or what the average blood glucose level is at morning, afternoon and evening hours.

Figure 2:
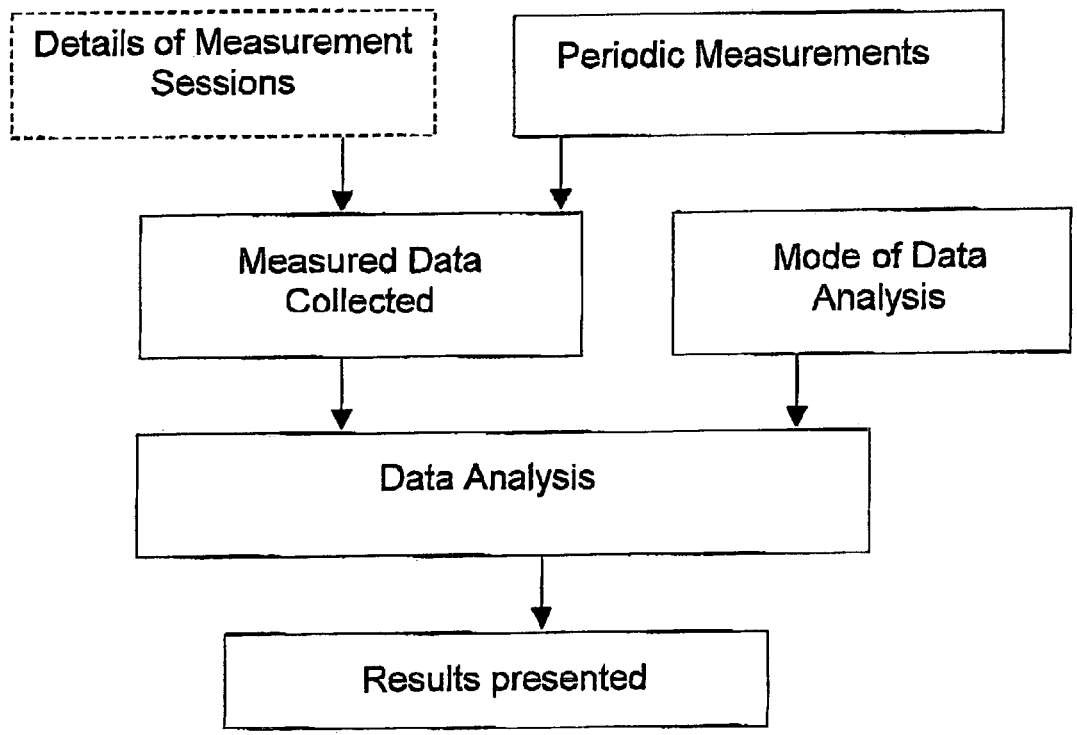
FIG. 2 is a flow chart of the steps of a self-monitoring method according to the invention.

FIG. 2 schematically shows the main steps in a method according to the invention. As shown, measurement sessions are carried out periodically (generally, non-continuously) during a day, and repeated during a predetermined period of time from several days to several weeks. As indicated above, these measurements may be initiated automatically, or manually by an individual himself. As shown in the figure in dashed lines, the method preferably also allows the patient to provide details about the measurement session (time of the day, time moment associated with a specific activity). Measured data indicative of the glucose levels corresponding to the measurement sessions, respectively, and preferably also of the details of the measurement sessions, are collected at the processor of the control unit. It should be understood that the measurement device can be designed such that the output data of the measurement unit is already representative of the blood glucose level, or alternatively, such that the output of the measurement unit is in the form of light/electrical response of the medium under measurements and is thus indicative of the blood glucose level which is to be calculated at the control unit. The collected measured data, and preferably also that entered by the patient, is analyzed by the processor utility in accordance with a mode of data analysis provided by the patient. The results are presented to the patient, for example in the form of a graph displayed on a monitor of the control unit or as a voice message.

Figure 3A:
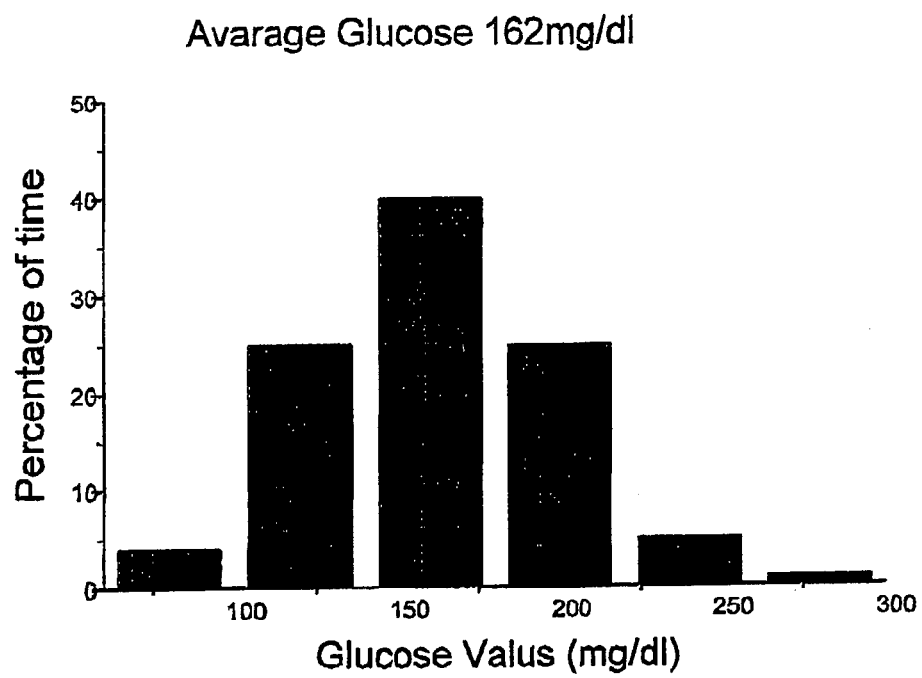
FIGS. 3A and 3B illustrate examples of the data analysis and results.
Figure 3B:
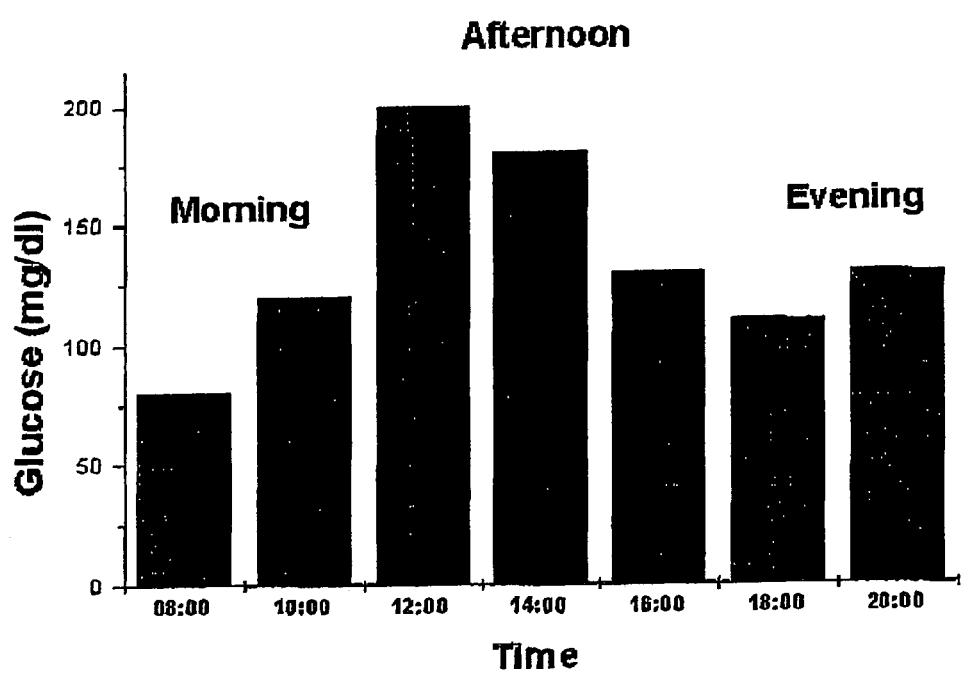

FIGS. 3A and 3B illustrate the data analysis and results according to two specific, but not limiting examples, of the invention.

In the example of FIG. 3A, the blood glucose levels distribution over time is presented, showing the percentage of occurrence of specific blood glucose levels over a certain period of time. In this specific example, 20 non-invasive measurements were taken within 2 days. As shown, most of the tie the patient's blood glucose level was at 162 mg/dl (euglycemic condition), at 4% of time it was at 100 mg/dl and less (hypoglycemic), and at 5% of the time it was at 220 mg/dl hyperglycemic), etc. The average blood glucose level over 2 days is about 162 mg/dl.

In the example of FIG. 3B, blood glucose level measurements periodically taken during 2 days are interpreted as a function of morning, afternoon, and evening hours. It can be seen that before lunch the glucose level was high relative to that of morning and evening hours.

It should be understood that, generally, the technique of the present invention may utilize invasive measurements, especially due to the fact that the technique of the present invention requires neither continuous measurements nor too many discrete measurements, and thus the measurement results need no additional correlation. Preferably, the technique of the present invention utilizes a combination of invasive and non-invasive measurements, or non-invasive measurements of two different kinds, namely, of higher and less precision of measurements requiring, respectively, longer and shorter time periods for data analyses and relatively complicated and simple measurement devices. For example, an invasive, or more precise non-invasive, measurement may be taken once a day (e.g., in the morning) and all the other measurements within at day are non-invasive (or more simple non-invasive measurement as compared to the first measurement). The control unit may thus be pre-programmed to take into account a difference between the measured data obtained with the first and second measurement devices to correlate between them, and calibrate accordingly the second device, which is used for carrying the sequence of measurements.

Figure 4A:
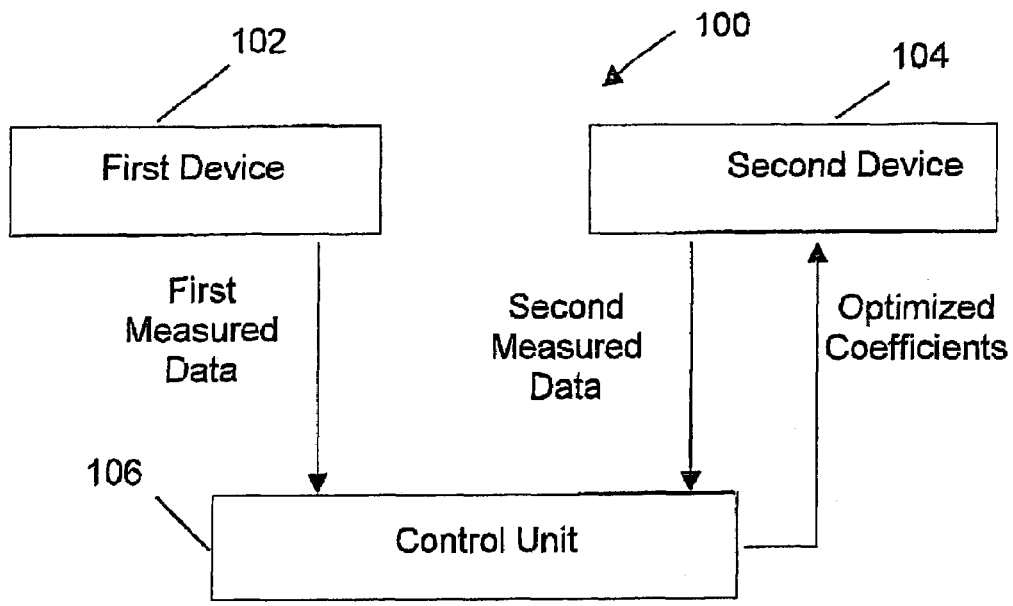
FIGS. 4A and 4B schematically illustrate the principles of an integrated technique of the present invention for calibrating a non-invasive measurement device.
Figure 4B:
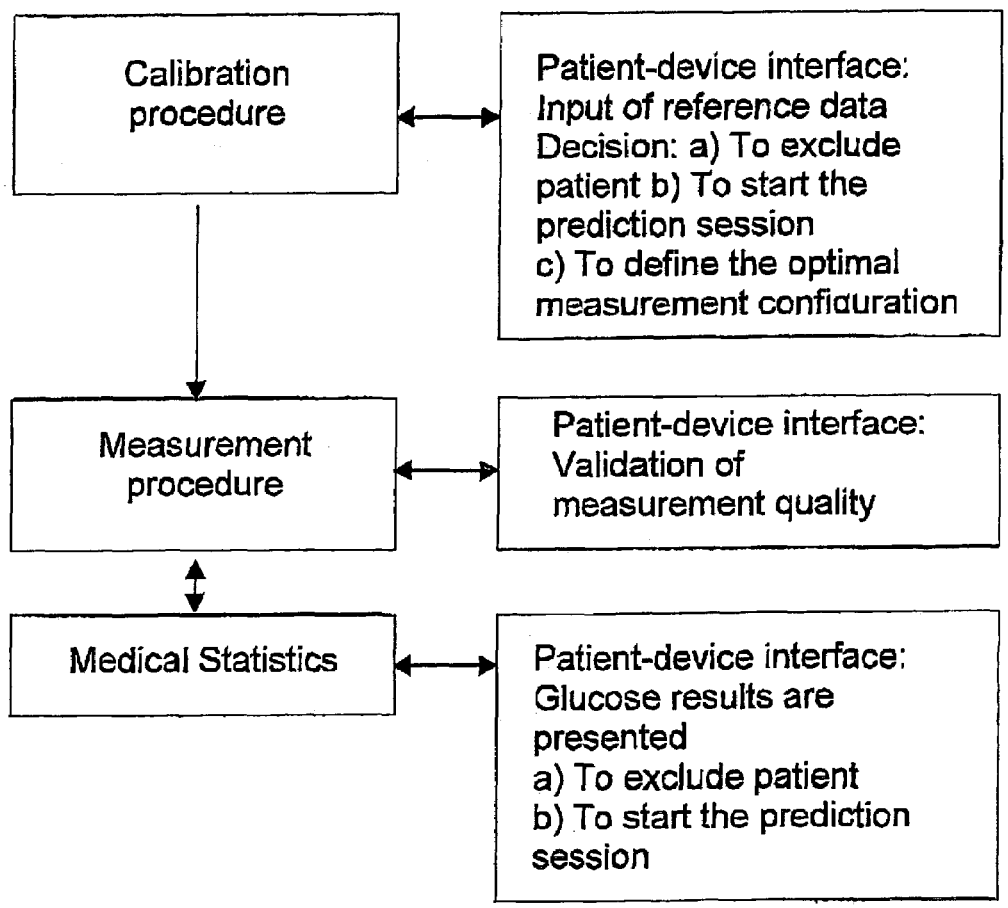

FIGS. 4A and 4B schematically illustrate such an integrated system 100 according to the invention utilizing a first measurement device 102 (say, invasive), a second non-invasive measurement device 104, and a control unit 106. The first (reference) measurement(s) taken with the first measurement device 102 are used for caring out the calibration procedure of the second measurement device. This is implemented by performing the first (reference) measurement with the deice 102 providing first measured data indicative of a "correct" value of the blood glucose concentration, and performing at least one second measurement with the device 104 operated either just prior to or immediately after the reference measurement (up to 15 minutes time interval between the first and second measurements). The control unit 106 is responsive to the first and second measured data to found a correlation between them, and apply a medical statistics algorithm (of any known suitable type, for example as disclosed in "Biostatistics in clinical medicine", J. Intelfinger et al, 1983, p.116-120) to optimize the coefficients (variables) used in a model utilized in the second measurement device for calculating the glucose concentration (e.g., in the processing of detected light responses) to obtain the best fitting between the first and second measured data. To this end, certain quality criteria are pre-defined for making the final decision upon meeting these criteria.

Figure 4C:
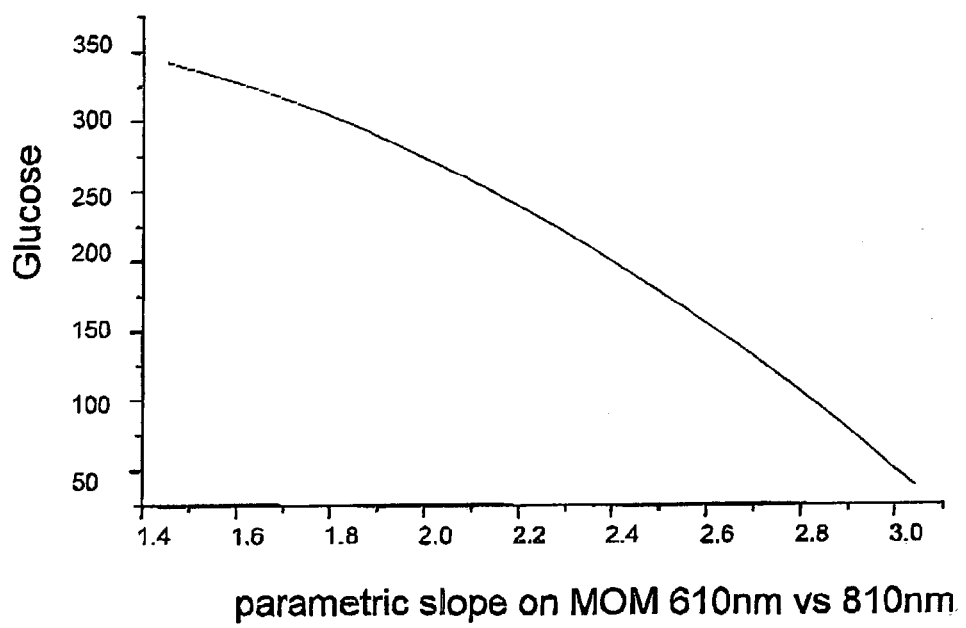
FIG. 4C illustrates a calibration curve obtained by applying numerous measurements with an integrator device of the present invention.

By applying numerous first, reference measurements and corresponding second measurements to a specific patient, a calibration function can be derived. Such a calibration fiction is exemplified in FIG. 4C. Generally, the calibration function is in the form of the glucose concentration value obtained with the first reference measurements as a function of measurement results obtained with the second non-invasive measurement device. In the present example of FIG. 4C, the second measurements are the occlusion-based measurements disclosed in the above-indicated U.S. patents. More specifically, the second measurements are multiple occlusion measurements (MOM) (i.e., periodical occlusion-release mode) with incident light of 610 nm and 810 nm wavelengths. The second measurement results are thus in the form of a parametric slope of a care calculated as the time changes of the light response at 610 nm as a function of the time changes of the light response at 810 nm. During further measurements, this calibration function can be updated. For example, a patient uses an invasive reference measurement in the morning and then sequentially applies the non-invasive measurements, while a control unit periodically analyses the first (reference) and second measured data and updates the calibration function.

The "simple" non-invasive measurement device may utilizes the application of pressure, e.g., occlusion-based measurements. This device may be used for measuring a patient's blood pressure, or preferably both the blood pressure and the glucose concentration in the patient's blood (abnormal blood pressure is one of the very widespread complications of diabetes mellitus).

Figure 5:
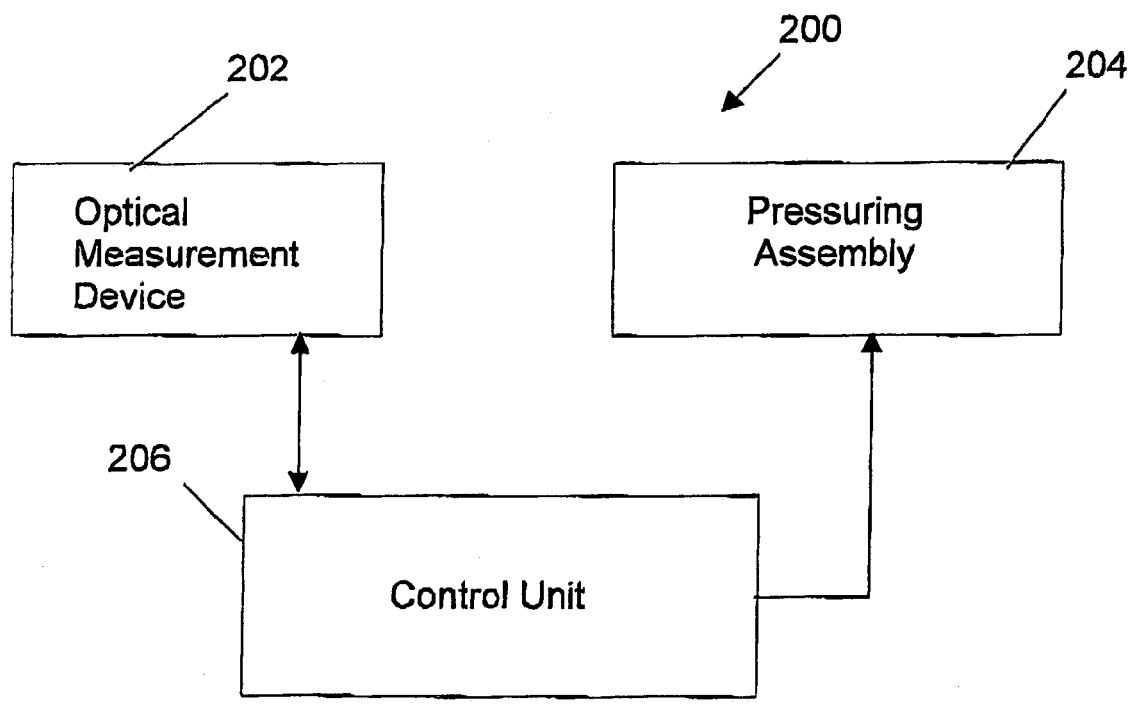
FIG. 5 illustrates a non-invasive measurement device according to the invention for measuring both the blood glucose concentration and the blood pressure.

FIG. 5 illustrates a non-invasive measurement 200 device according to the invention utilizing the above concept. The device comprises a pressurizing assembly 202, an optical measurement system 204, and a control unit 206. The control unit operates the pressurizing assembly to apply pressure to the patient's blood perfused fleshy medium gradually increasing up to over-systolic pressure, and concurrently operates the optical measurement device to detect the time variations of a light response of the medium at different values of the applied pressure.

Figure 6A:
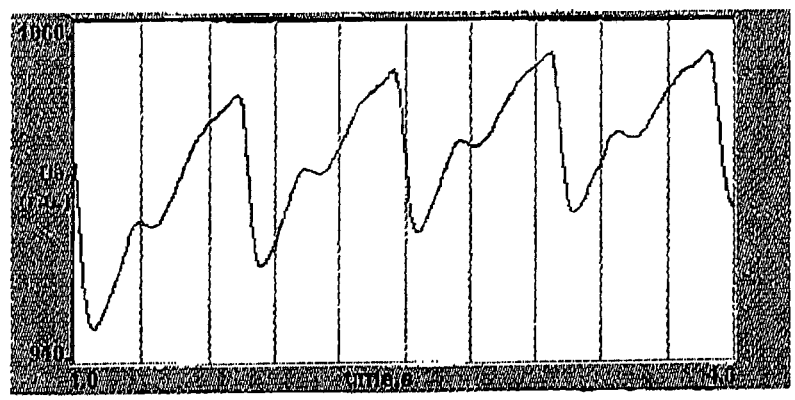
FIGS. 6A to 6H illustrates the experimental results of using a method of the present invention for measuring the patient's blood pressure.
Figure 6B:
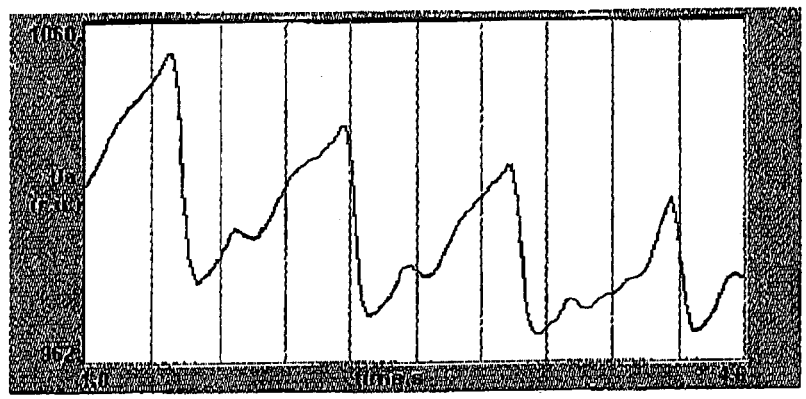
Figure 6C:
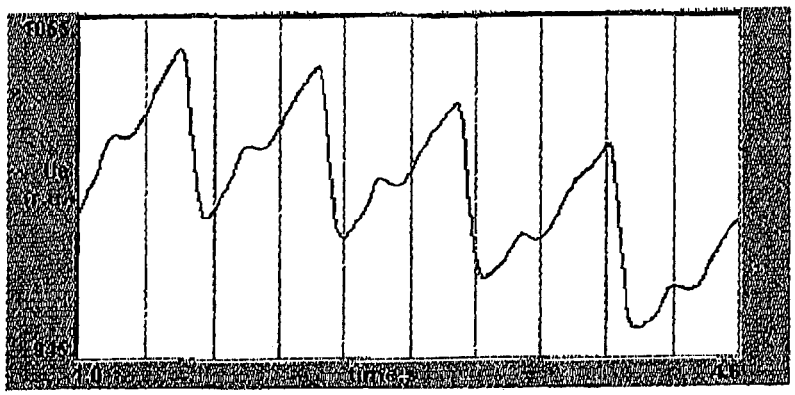
Figure 6D:
Figure 6E:
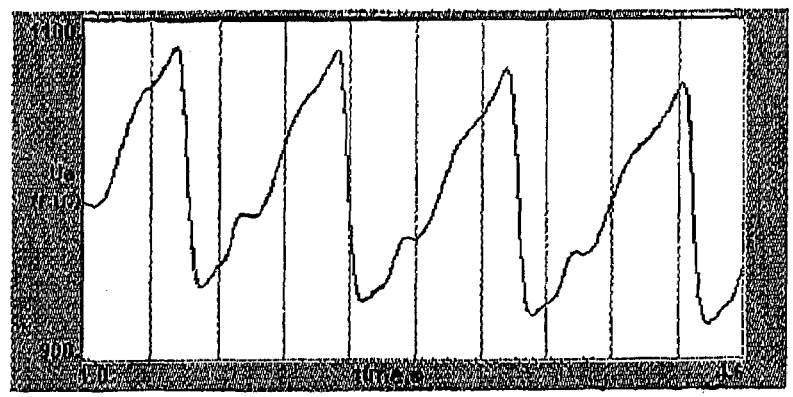
Figure 6F:
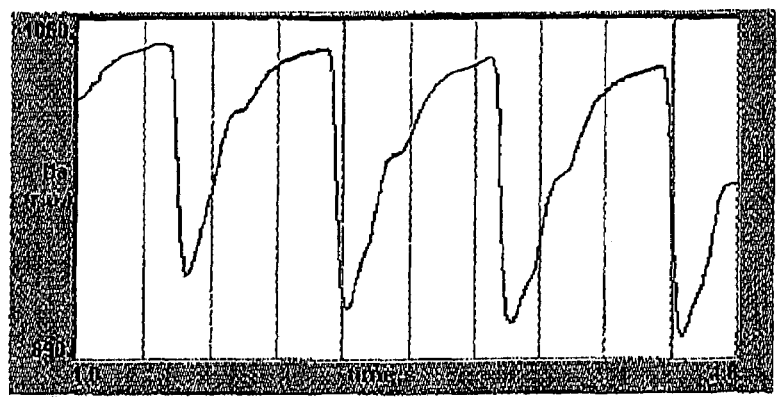
Figure 6G:
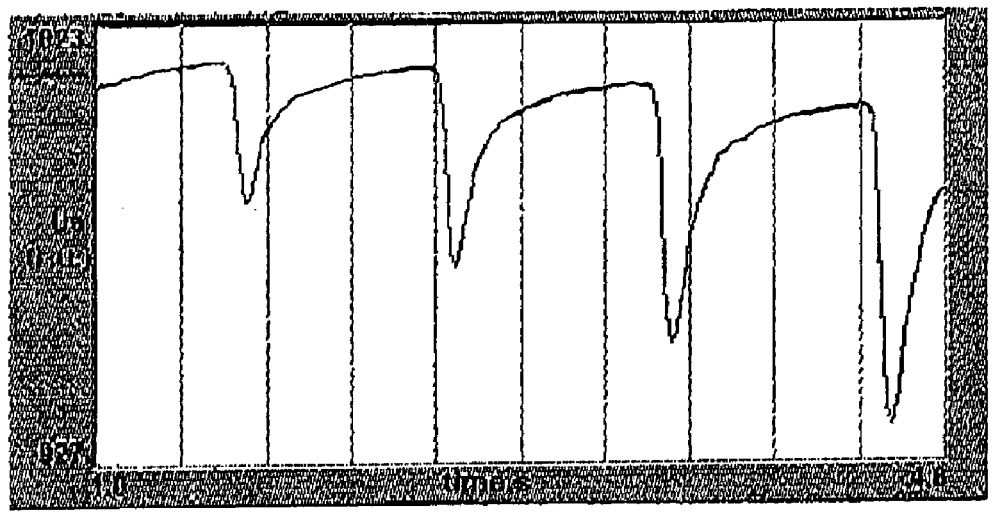
Figure 6H:
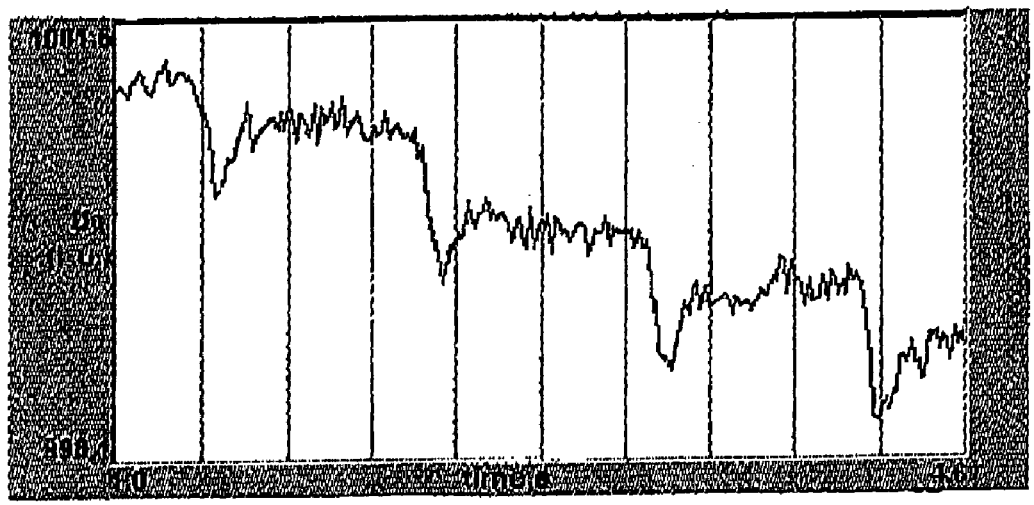

The measurement results are illustrated in FIGS. 6A-6H showing the light response profiles (i.e., time variations of the light responses) obtained with 610 nm wavelength of incident light at different values of pressure: $P_1=0$ (FIG. 6A), $P_2=15$ mmHg (FIG. 6B); $P_3=30$ mmHg (FIG. 6C); $P_4=45$ mmHg (FIG. 6D); $P_5=55$ mmHg (FIG. 6E); $P_6=65$ mmHg (FIG. 6F); $P_7=90$ mmHg (FIG. 6G); and $P_8=130$ mmHg (FIG. 6H). As shown, with no applied pressure (FIG. 6A) and at pressure values $P_2$-$P_7$ (FIGS. 6B-6G), the light response profiles have clearly pronounced pulsatile components. At lower pressure values $P_2$-$P_5$, the light response profiles have very similar forms, while at the pressure value $P_6$ (FIG. 6F) the form of the light response profile changes. This pressure value $P_6=65$ mmHg corresponds to the blood diastole. At pressure value $P_8$ (FIG. 6H), the pulsatile components practically disappear. This over-systolic pressure $P_8=130$ mmHg corresponds to the blood systole for this specific patient.

A pressure above said systolic pressure $P_8$ is then applied and maintained during a certain time period to cause the creation of a state of blood flow cessation in the medium. Then, the control unit operates the optical measurement system to apply optical measurement sessions with different wavelengths of incident light (at least two wavelengths) while at the blood flow cessation state, thereby measuring the light response profiles (time variations of the light response) for different wavelengths of light, and the glucose concentration related measured data is obtained from a relation between these two different light profiles, taken at the same pressure but different wavelengths of light. This technique is disclosed in the above-described US patents assigned to the assignee of the present application.

The invention claimed is:

1. A method of self-monitoring a patient's blood glucose condition to determine a long-term effect of the patient's behavior on his blood glucose level, the method comprising: collecting measured data during a predetermined time period while taking a sequence of measurements of the blood glucose level during a day and repeating the sequence of measurements from several days to several weeks, said sequence of measurements including non-invasive-measurements utilizing application of pressure to the patient's blood perfused fleshy medium, said application of pressure including application of over-systolic pressure thereby causing a state of temporarily blood flow cessation in the medium, the measured data being in the form of time variations of light responses of the medium to incident light for at least two different wavelenghts of the incident light, respectively;

analyzing the measured data to determine a relation between changes in the two time variations indicative of the glucose concentration in the patient's blood, and determine a distribution of average glucose values within said predetermined time period, and presenting results of the determined distribution of the average glucose values in a visual or auto format to the patient or an authorized person.

2. The method of claim 1, comprising calibrating a non-invasive measurement device used for carrying out said sequence of measurements.

3. The method of claim 2, wherein said calibrating comprising using a first measurement device, of a kind different from said non-invasive measurement device, to perform at least one first reference measurement and obtain first measured data of blood glucose concentration for a specific patient; applying said non-invasive measurement device to said patient to perform at least one of the non-invasive measurements either prior to or after said first measurement, and determining second measured data indicative of the glucose concentration in the patient's blood while utilizing a certain calculation model; and determining a correlation between said first measured data and said second measured data, and applying a statistic algorithm to thereby optimize coefficients used in said model to obtain the best fitting between the first and second measured data.

4. The method of claim 3, wherein said first measurement device is designed to carry out invasive measurements.

5. The method of claim 3, comprising carrying out a plurality of the reference measurements and calculating a calibration function.

6. The method of claim 5, comprising utilizing data obtained during further measurements with the first and second measurement devices and updating the calibration function.

7. The method of claim 1, comprising measuring a patient's blood pressure, the method comprising:

applying to the patient's blood perfused fleshy medium a gradually increasing pressure, and concurrently applying optical measurements to the medium to determine a time variation of a light response of the medium as a function of the applied pressure;

analyzing the measured time variations of the light response as the function of the applied pressure to determine a diastolic pressure as the pressure corresponding to an appearance of a changed form of the time variation of the light response while having pulsatile components and determine a systolic pressure as the pressure corresponding to substantial disappearance of the pulsatile components in the time variation of the light response.

8. A measurement device for use in self-monitoring a patient's blood glucose condition, the device comprising: a measurement unit configured to be operable for carrying out non-invasive-measurements by applying over-systolic pressure to patient's blood perfused fleshy medium thereby causing a state of temporarily blood flow cessation in the medium, applying optical measurements with at least two different wavelengths of incident light to the medium while at the state of blood flow cessation to detect time variation of a light response of the medium for each of said at least two wavelenghts, and generating measurable data indicative thereof; and a control unit connectable to the measurement unit, the control unit being configured for operating the measurement unit during a predetermined time period for taking a sequence of measurements, including said non-invasive measurements, during a day and repeating the sequence of measurements from several days to several weeks, and being configured and operable for collecting the measured data, analyzing the collected measured data to determine a relation between changes in the two time variations indicative of the glucose concentration in the patient's blood, determine a distribution of average glucose values within the predetermined time period, and presenting results of the determine a distribution of the average glucose values in a visual or audio format the patient or an authorized person, said presented results being indicative about a long-term effect of the patient's behavior on his blood glucose level.

9. A non-invasive measurement device comprising:

an optical measurement system for applying to a patient's blood perfused fleshy medium, said system including an illuminator producing light of at least two different wavelengths, and a light detector for detecting light responses of the medium at the different wavelengths and generating measured data indicative thereof;

a pressurizing assembly operable to apply pressure to the medium; and a control unit configured for operating the pressurizing assembly to apply gradually increasing pressure to the medium, and maintaining the application of pressure during a certain time period upon reaching certain over-systolic pressure, and for operating the measurement system to apply measurements and generate the measured data during the application of pressure, the control unit having a data processing and analyzing utility operable to analyze the light responses and determine a diastolic pressure as the pressure corresponding to an appearance of a changed form of the light response profile while having pulsatile components, determine a systolic pressure as the pressure corresponding to substantial disappearance of the pulsatile components in the light response profile, and determine the glucose concentration from a relation between the light response profiles at the different wavelengths measured during the application of said certain over-systolic pressure.

10. A method of self-monitoring a patient's blood glucose condition to determine a long-term effect of the patient's behavior on his blood glucose level, the method comprising:

applying to the patient's blood perfused fleshy medium a gradually increasing pressure, and concurrently taking optical measurements of the blood glucose level on the medium and collecting measured data during a predetermined time period including a sequence of measurements taken during a day and repeated sequence of measurements taken during a period from several days to several weeks, the measured data being in the form of a time variation of a light response of the medium as a function of the applied pressure;

analyzing measured data to determine a distribution of the average glucose values within said predetermined time period, thereby providing a feedback for the patient or an authorized person, and to determine a diastolic pressure as the pressure corresponding to an appearance of a changed form of the time variation of the light response while having pulsatile components and determine a systolic pressure as the pressure corresponding to substantial disappearance of the pulsatile components in the time variation of the light response;

presenting results of the determined distribution of the average glucose values and the diastolic and systolic pressures, in a visual or audio format to the patient or an authorized person.

* * * * *